United States Patent [19]

Peck et al.

[11] Patent Number: 4,803,744
[45] Date of Patent: Feb. 14, 1989

[54] INFLATABLE BED

[75] Inventors: William H. Peck, Oldenburg; Michael E. Poehner, West Harrison, both of Ind.

[73] Assignee: Hill-Rom Company, Inc., Batesville, Ind.

[21] Appl. No.: 52,676

[22] Filed: May 19, 1987

[51] Int. Cl.$^4$ .............................................. A47C 27/10
[52] U.S. Cl. ............................................. 5/453; 5/455
[58] Field of Search ................... 5/453, 454, 469, 449, 5/455, 456

[56] References Cited

U.S. PATENT DOCUMENTS

| 3,644,950 | 2/1972 | Lindsay . | |
|---|---|---|---|
| 3,653,083 | 4/1972 | Lapidus | 5/469 |
| 3,674,019 | 7/1972 | Grant | 128/33 |
| 3,822,425 | 7/1974 | Scales | 5/456 |
| 4,193,149 | 3/1980 | Welch | 5/453 |
| 4,224,706 | 9/1980 | Young et al. | 5/455 |
| 4,225,989 | 10/1980 | Corbett et al. | 5/453 |
| 4,394,784 | 7/1983 | Swenson et al. | 5/453 |
| 4,435,864 | 3/1984 | Callaway | 5/453 |
| 4,525,885 | 7/1985 | Hunt et al. | 5/455 |

Primary Examiner—Alexander Grosz
Attorney, Agent, or Firm—Steve M. McLary; F. Kristen Koepcke

[57] ABSTRACT

This invention is concerned with an improved air bed system. In this invention, the bed occupant can control the firmness of the bed. Two inflatable bladders are used with a pre-set pressure differential between them. The pressure in the lower bladder is always kept high enough to prevent bottoming of a bed occupant. The pressure in the upper bladder can be adjusted by the occupant to his or her own personal comfort level. The invention may also include various medical devices which are fluid powered, thus taking advantage of the presence of the pressurized working fluid. The invention may further include a warning circuit which senses the departure of an occupant from the bed and generates a warning signal in response thereto.

28 Claims, 4 Drawing Sheets

INFLATABLE BED

BACKGROUND OF THE INVENTION

The use of various types of air beds for both comfort and therapeutic purposes is known in the art. These have tended to be expensive and somewhat inflexible in their ability to adjust to patient demands. That is, most of the prior art beds are designed to perform a particular purpose and their feel or firmness to a person lying on them is not adjustable.

Hospital patents, in particular, complain about the uncomfortable nature of standard mattresses. Yet the air beds of the prior art are usually too expensive for general use throughout a hospital and in any case are not usually flexible enough in operation to allow comfort adjustment by the patient. There has been a need for a sleep and support surface whose firmness can be adjusted by the occupant.

The following U.S. patents are cited to show air beds whose firmness may be controlled by the occupant: U.S. Pat. Nos. 4,224,706; 4,394,784; and 4,435,864. U.S. Pat. Nos. 3,822,425 and 4,525,885 show forms of air beds specifically designed for medical purposes. U.S. Pat. Nos. 3,653,083; 3,674,019; 4,193,149; and 4,225,989 all show dual bladder air mattresses.

The present invention provides a patient controllable air bed that has built in control features that prevent "bottoming". In the case of some air beds, the user may deflate it so much, in an attempt to obtain a softer rest surface, that he may eventually overcome the supportive effects of the air bed and hit the hard support surface under the mattress. This is clearly undesirable and the present invention prevents this through a differential pressure control system between upper and lower bladders.

SUMMARY OF THE INVENTION

This invention relates to an improved inflatable bed system, in particular an air bed, and a method for controlling its operation. The inflatable bed includes a first inflatable bladder that is remote or distal from a person who occupies the bed. A second inflatable bladder is positioned proximate or next to a person who occupies the bed. The second bladder also is positioned to touch, nest with and overlie the first bladder. Also provided is a source of inflating fluid, preferably air, at a pressure sufficient to inflate the two bladders to the degree necessary to support a person lying on them. The bed system also includes a fluid circuit that interconnects the bladder to the source of pressurized fluid. The fluid circuit controls the flow of the inflating fluid in such a manner that a pre-selected pressure differential is maintained between the first and second bladders, this pressure differential being selected so that the lower or first bladder is always at a higher pressure than the upper or second bladder. This pressure in the lower bladder is selected so that an occupant of the bed cannot reduce the total bed pressure sufficiently to "bottom out". This allows adjustment of the pressure in the upper or second bladder to change the feel or comfort of the bed within a wide range to allow for occupant preferences without the danger of allowing the entire bed pressure to drop below that which would support an occupant. The fluid circuit also controls inflation of the bladders so the first bladder always is partially inflated before inflation of the second bladder begins.

DETAILED DESCRIPTION OF A PREFERRED EMBODIMENT OF THE INVENTION

This invention is directed toward providing an improved form of resting surface, primarily for hospitalized patients. However, the basic air bed system which is described could be used for normal sleep purposes, and is not necessarily limited to a hospital environment. Therefore, while the description that follows will be primarily directed toward hospital usage, it should be kept in mind that the invention itself is not necessarily so limited.

Figure 1:
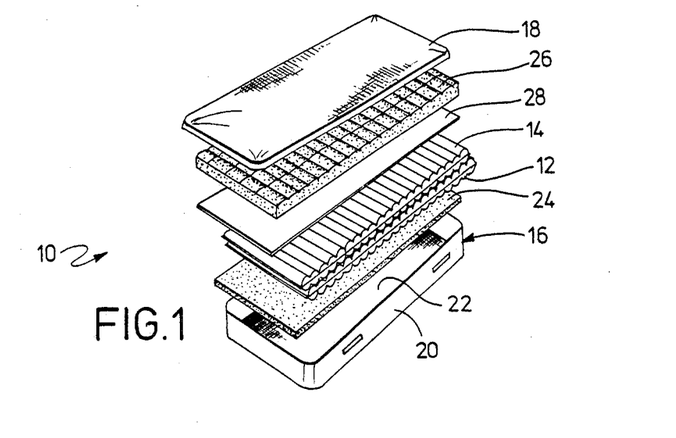
FIG. 1 is an exploded perspective view of the mattress portion of the present invention.

FIG. 1 illustrates the mattress portion 10 of the air bed system of the present invention. The primary components of the mattress 10 are two independent inflatable bladders 12 and 14. The first bladder 12 in its normal operating position is located at a position distal or away from a person who would lie on the mattress 10. The second inflatable bladder 14 is positioned to be in contact with the first bladder 12 and is also positioned so that it would be proximate or adjacent to a person who was lying upon the mattress 10. It is important that the two bladders 12 and 14 be maintained in general contact with one another during the use of the mattress 10. To this end, several possible configurations are possible, but that shown in FIG. 1 is preferred. A configuration of the mattress 10 as shown in FIG. 1 will be described in some detail, but it should be kept in mind that the other components of the mattress 10 shown in FIG. 1 basically serve as a means for holding the first bladder 12 and the second bladder 14 together so that they cooperate as a unit. Other measures such as straps, adhesives, clips or other types of fasteners could be used.

The mattress portion 10 includes a casing which is made up of a lower portion 16 and an upper portion 18. The casing is preferably made of a fabric material that is relatively flexible to allow easy insertion of the various components that make up the mattress portion 10. A suitable material is a nylon fabric with coatings on both sides. The coatings are those which are common for use in a hospital environment to prevent penetration of both liquids and bacteria. The fabric may also be coated with a flame retardant chemical. There are various forms of bacterial and viral control agents which can be added to the fabrics for use in a hospital environment, and these may also be added to the casing of the mattress 10. The lower portion 16 is preferably generally box shaped with an upstanding perimeter wall 20 which is bonded to a base portion 22. As can be seen from FIG. 1, the internal components of the mattress 10 are inserted into the lower portion 16 and are generally held in place by the perimeter wall 20. The upper portion 18 is then attached to the perimeter wall 20 to form a complete mattress portion 10. This joining of the upper portion 18 to the perimeter wall 20 may be achieved in any one of several known and conventional ways. Conventionally, this joinder is made by means of a zipper which extends around the outside of the perimeter wall 20, but the joinder could also be made by means of releasable fabric fasteners such as those sold under the trade name VELCRO. A suitable means, such as conduits 68 and 80, extend through the perimeter wall 20 to allow the introduction of working fluid to the bladders 12 and 14.

It is preferred that the mattress portion 10 also include some other components, particularly in the case of the mattress 10 which is to be used in a hospital environment. A lower foam pad 24 may be inserted in the lower portion of the casing 16 in a position below the first inflatable bladder 12. Preferably, this lower foam pad 24 is approximately one inch in thickness and is of a polyurethene foam. Also, an upper foam pad 26 is preferred. The upper foam pad 26 is preferably placed immediately below the upper portion 18 of the casing and is approximately two inches in thickness. This upper foam pad 26 is also preferably a polyurethene foam. A final component of the mattress portion 10 which is particularly well suited for use in a hospital environment is a needle barrier 28. The needle barrier 28 is a sheet of material which is placed between the upper foam pad 26 and the second inflatable bladder 14. It is known that in a hospital environment, needles or attachment pins are sometimes inserted into the mattress upon which the patient is lying. In most cases, this causes no particular problem because the mattresses are of a foam or similar construction which are not harmed by needle entry. In the present case, repeated entry of needles into the inflatable bladders 12 and 14 could eventually lead to failure of these bladders by uncontrolled leakage. Thus, the needle barrier 28 is preferred for use in the hospital environment and is a material such as 1/16th inch cloth reinforced neoprene rubber, polypropylene or similar materials. It is designed to be coextensive with the surface of the second inflatable bladder 14. Thus, any needle must pass through the two inch upper foam pad 26 and then penetrate the needle barrier 28 before it could enter the second inflatable bladder 14.

Figure 2:
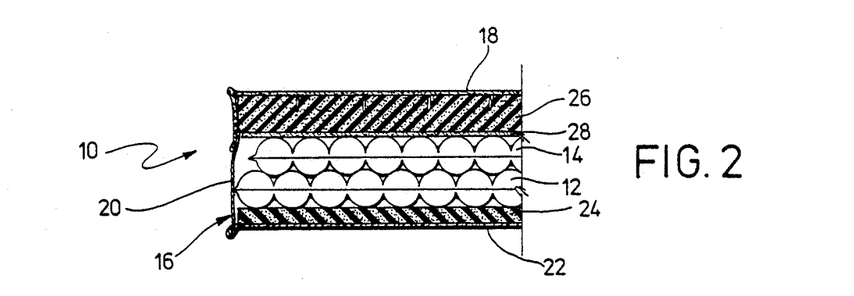
FIG. 2 is a partial side elevation cross section of the mattress portion shown in FIG. 1 in its assembled state.

The cross-sectional view of FIG. 2 illustrates the mattress portion 10 in a completely assembled configuration. FIG. 2 also shows the mattress portion 10 in its fully inflated configuration as it would normally be in use. Note that the bladders 12 and 14 are of a convoluted shape made of a series of transverse ribs which allow the unit to articulate rather easily with the movement of a hospital bed. Also note that the first and second bladders 12 and 14 are positioned such that their respective ribs nest together which allows for close contact and support of a person lying on the mattress portion 10. The transverse ribs extend, in normal use, across the transverse dimension of a bed.

Figure 3:
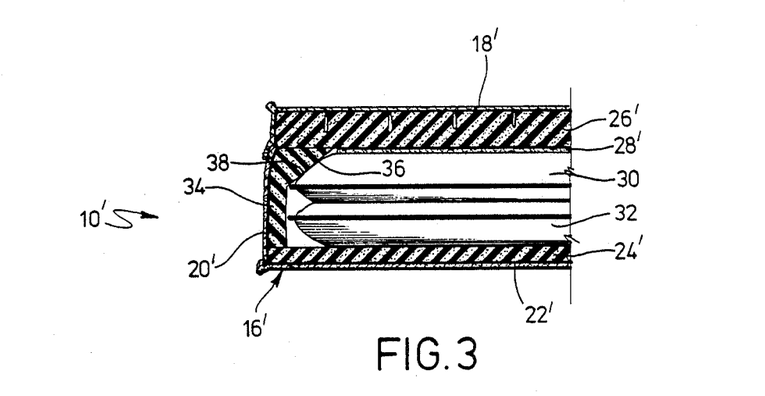
FIG. 3 is a partial side elevation cross section of a modified embodiment of the mattress portion of the present invention.

FIG. 3 illustrates a mattress portion that is somewhat modified from that shown in FIGS. 1 and 2. Since many of the components between FIGS. 2 and 3 are the same, those components which are the same are identified by prime numerals as for example mattress portion 10' and only those new or modified elements are given new numerals. Mattress portion 10' of FIG. 3 still includes an upper casing portion 18' and a lower casing portion 16' with perimeter wall 20' and base portion 22'. The upper portion 18' is attached to the perimeter wall 20' as was the case in FIGS. 1 and 2. The mattress 10' also includes an upper foam pad 26', a lower foam pad 24' and preferably a needle barrier 28'. The primary distinction in the mattress 10' shown in FIG. 3 is that the inflatable bladders designated as 12 and 14 in FIG. 2 and having a transverse rib portion have been replaced by generally flat or flattened bladders 30 and 32. As was noted, the bladders 12 and 14 previously shown are preferred for use in a hospital environment because their transverse rib configuration allows somewhat easier articulation with a hospital bed. On the other hand, in a situation where articulation of the mattress portion is not required, bladders such as 30 and 32 are somewhat less expensive to make and thus could be usable while still providing much of the benefit of the present invention.

Another aspect of this invention is also illustrated in FIG. 3 with respect to the use of foam inserts at the perimeter of the mattress portion 10'. The foam inserts 34 extend around the perimeter of the upstanding perimeter wall 20' and essentially completely enclose the bladders 30 and 32. Note that the upper portion 36 of the upper bladder 30 is tapered and the foam portion 34 tapers inwardly to meet this tapered portion 36. The purpose of the foam insert 34 is to give a fairly rigid feel to the perimeter of the mattress 10' even though the bladders 30 and 32 may be almost completely deflated. The tapering portion 36 and its corresponding tapered portion 38 of the foam insert 34 work together to form an additional needle barrier to prevent needle sticks coming from the side of the mattress portion 10'. That is, it can be seen that the foam insert 34 acts as something of a barrier for needles which come from the side, but the tapered portion 38 provides an even greater barrier to such accidental insertion of needles. Comparing FIG. 3 with FIG. 2, one can see that the sides of the bladders 12 and 14 in FIG. 2 are relatively exposed to accidental needle punctures from the side. The foam insert 34 could be used in the configuration shown in FIG. 2, but the use of this insert renders the entire mattress portion somewhat less flexible, and thus somewhat less usable for articulation in a hospital bed.

Figure 4:
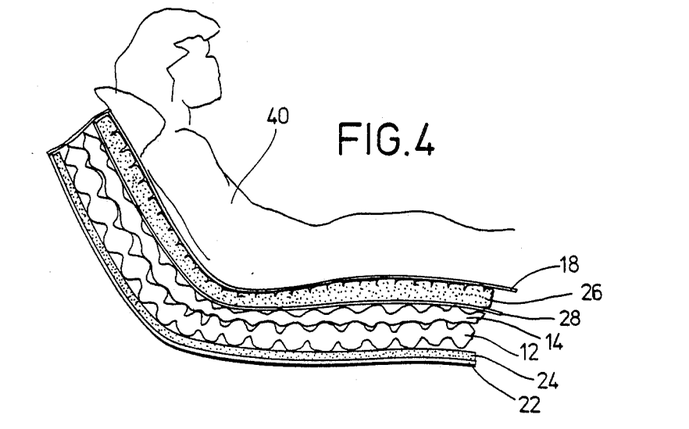
FIG. 4 is a partial side elevation cross section showing the functioning of the mattress portion of the present inventions when the mattress is articulated or bent.

FIG. 4 illustrates the bending of the mattress portion 10 when it is placed in a hospital bed environment and articulated with a patient 40 placed on the mattress portion 10. Note that what occurs is that the first bladder 12 retains a relatively fixed degree of inflation, while the second bladder 14 has a somewhat varying configuration dependent upon where it is along the length of the distribution of the patient's weight. It is this ability to conform and change with respect to the movement of a patient that is believed to be the most important characteristic of the present invention. The aim of the present invention is to allow a patient or any person who lies upon such an air bed assembly the ability to control the firmness of the bed. This ability to adjust the firmness of the bed is believed to be quite important for patient or occupant comfort. While clinical proof is as yet unavailable, it is believed that the present invention may also have some beneficial affect in the prevention of decubitus ulcers or bed sores. These ulcers are a particularly difficult problem for hospitals to deal with with respect to immobilized patients. This is so because pressure for a prolonged period on bony prominances of the body tend to produce these ulcers. A standard hospital bed mattress may exert 50 to 60 millimeters of pressure on a body lying upon it. Capillary pressure for a human being is in the range of 30 to 32 millimeters of mercury. It can easily be seen that capillary restrictions from a standard mattress will result in a decreasing blood flow and the possible formation of decubitus ulcers. Of course, decubitus ulcers generally can be prevented by proper assessment of the patient, correct diet, proper incontinence care and the use of pressure reduction aids and devices and frequent turning. None the less, this is a persistent problem in the hospital environment and air bed systems such as those shown in the present invention are believed to be of assistance in reducing the incidence of such ulcers.

Figure 5:
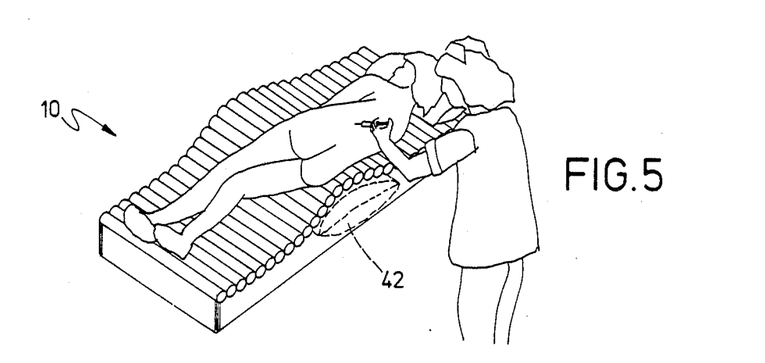
FIG. 5 is a perspective view of the use of a medical procedure pad with the present invention.

FIG. 5 illustrates that with the flexibility of the mattress portion 10 and the availbility of a source of compressed air, some medical procedures become easier than was previously the case. FIG. 5 illustrates the administration of a spinal block anesthetic. At the present time, pillows are used to raise the patient's midsection to a position where the vertebra of the patient's spine is compressed from one side and opened on the other. This is awkward in operation and FIG. 5 illustrates a procedure using the mattress portion 10 of the present invention which would make this easier. An inflatable procedure pad 42 is inserted in the midsection of the mattress portion 10 preferably under the first inflatable bladder 12. Then, as can be seen in FIG. 5, when the procedure pad 42 is inflated, it bulges the midsection of the mattress 10 and by proper positioning of the patient on the mattress, the desired access to the spinal region can be achieved.

Figure 6:
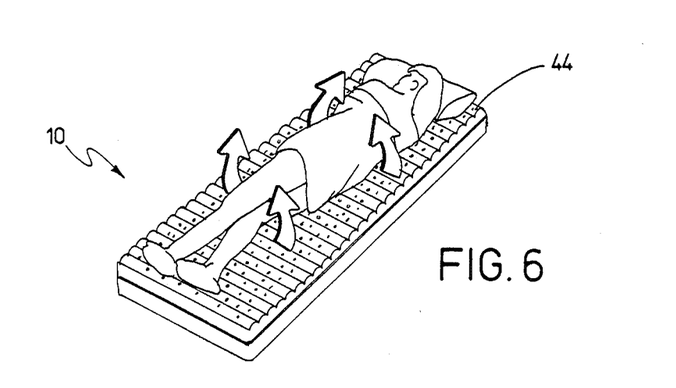
FIG. 6 is a perspective view of the present inventions with the addition of a perforated upper bladder that washes an occupant of the bed with an air flow.

FIG. 6 illustrates the fact that having a source of compressed air or other gas available makes it possible to provide so called clinically active elements to the patient using this bed in a hospital environment. For example, the upper foam pad 26 could be replaced with a perforated air bladder such as that shown at 44 in FIG. 6. The perforated bladder 44 is of the type which is known in the art to which a continual supply of air is fed. The air then passes upward through the perforated air bladder 44 and flows around the body of a person lying on the bladder 44. If desired a sheet or other covering could be placed over the bladder 44. This would not interfere with the air flow so long as the covering is gas permeable. This air then carries away moisture and heat from the body. The air may be from the supply used to inflate the bladders 12 and 14 or maybe a second supply which is filtered and heated and/or cooled as may be required by the needs of a person occupying the bed.

Figure 7:
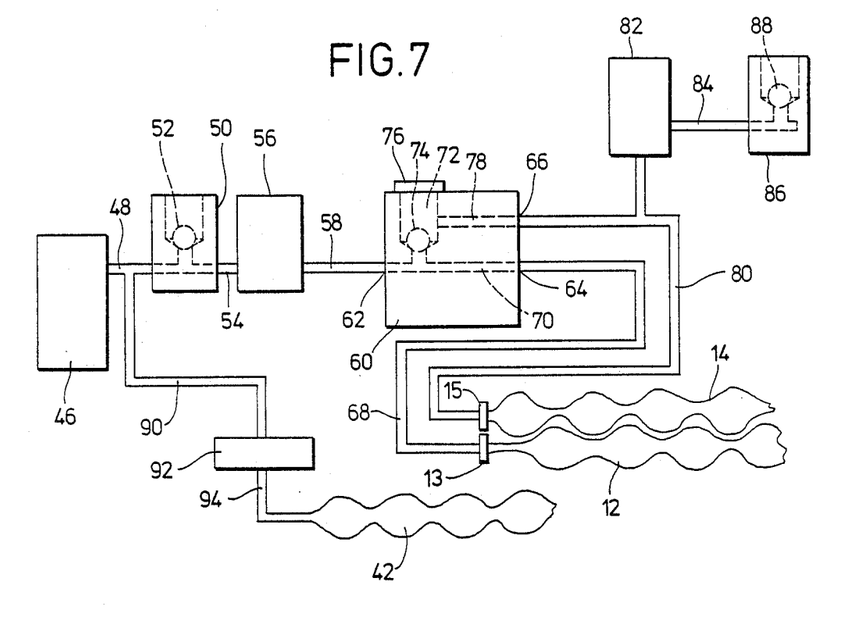
FIG. 7 is a schematic circuit diagram of the fluid circuit of the present invention.

FIG. 7 illustrates the fluid supply and control circuit of the present invention. The circuit shown in FIG. 7 includes a source of inflating fluid under pressure and a circuit means connected to bladders 12 and 14 to control the flow of the inflating fluid such that the bladder 12 is always inflated before the bladder 14 and the bladder 12 always has a higher pressure in it than the bladder 14. In the present invention, air is preferred as the working fluid. Thus, a small air compressor 46 may be used. The air compressor 46 is a source of inflating fluid at a pressure sufficient to inflate the bladders. The air compressor 46 is preferred as opposed to a high volume but lower pressure device because this particular invention does not involve the continual loss of air as do some other air beds currently used for medical purposes. Thus, once pressure is established in the bladders 12 and 14, is is usually maintained. A preferred air compressor 46 is a free piston type pump. The air compressor is connected by a suitable conduit 48 to a maximum pressure control valve 50. The maximum pressure control valve 50 is optional, but it is preferred because as well as serving as a safety valve to control the maximum pressure which can be supplied to the system, it also acts as a maximum firmness control valve. Thus, the pressure control 50 is a valve of the type in which a ball 52 is positioned internally of the valve 50 and has a particular pre-selected weight. So long as the pressure supplied to the valve 50 does not exceed the pre-selected force required to lift the ball 52, the fluid will be supplied through the conduit 48 and passed through the valve 50 unaffected. However, should the pressure supplied either through the conduit 48 or as a function of back pressure to valve 50 exceed the pre-set pressure controlled by the ball 52, the ball 52 will rise from its seat within the valve 50 and allow air to escape to the atmosphere through the valve 50 until the pre-set pressure is re-established. While shown as a pre-selected weight ball 52, a spring could also be inserted on top of the ball 52 and adjusted to allow adjustment of the maximum firmness of the bladders 12 and 14. This would also have a tendency to establish or control the maximum inflation pressure within the entire system. If one were to desire additional complexity, a pressure sensor could be placed in the conduit 48 with a pre-set pressure limit. Exceeding this pre-set pressure limit could then trigger a solenoid type valve which would allow bleeding of air from the conduit 48 until the pre-set pressure had been reached.

Fluid is then transferred from the pressure control valve 50 through a conduit 54 to an inflation control valve 56. The inflation control valve 56 is preferably a solenoid type valve whose operation is controlled either by a patient using this particular bed or by a nurse or other medical person who wishes to actuate the controls of this invention. Actuation of the control valve 56 and the air compressor 46 will allow air to flow through the conduits 48, 54 and the valve 50 through the inflation control valve 56 and into a conduit 58. The inflation control valve 56 could be a simple check valve. In that case, then only the air compressor 46 would need to be actuated to begin the inflation process. The conduit 58 is then connected to a differential pressure control valve 60, which is very important part of the present invention.

The differential pressure control valve 60 is so configured that it will always allow inflation of the first inflatable bladder 12 prior to the inflation of the second inflatable bladder 14. In addition, it is pre-set so that the pressure in the first bladder 12 will always be greater than in the second bladder 14. This differential pressure between the two bladders, 12 and 14, provides the beneficial effects previously noted and allows independent adjustment of occupant comfort of the mattress 10. The conduit 58 is connected to the single inlet 62 of the pressure control valve 60. The pressure control valve 60 has two outlets. 64 and 66. The first oulet 64 is connected through suitable conduit 68 to the first inflatable bladder 12. The conduit 68 would preferably be a flexible material which would allow easy routing of the conduit 68 in its path from the control valve 60 to the inflation inlet of the bladder 12. The outlet 64 of the differential valve 60, allows operating fluid to pass through the pressure control valve 60 essentially unchanged. That is, the operating fluid supplied through the conduit 58 into the inlet 62 of the valve 60 passes directly out through the outlet 64 and thence through the conduit 68 to the bladder 12. The conduit 68 is preferably connected to the bladder 12 through a conventional quick disconnect coupling 13. The coupling 13 is of the type which will trap pressure in the bladder 12 if the conduit 68 is removed. This can be used to allow shipping the entire mattress portion 10 with the bladders 12 and 14 partially inflated for ease of handling. As the operation of this device begins, the flow of operating fluid out of the second outlet 66 is blocked. All of the fluid entering the valve 60 will exit through the outlet 64 and thus inflate the bladder 12.

The differential pressure control valve 60 functions through the use of a controlled weight steel ball. The inlet 62 is connected to an internal passage-way 70, which is directly connected to the first outlet 64. Connecting to the passage way 70 is a control ball chamber 72, in which a steel ball 74 is positioned in such a way as to normally block off communication between the control ball chamber 72 and the passage way 70. A cap 76 is used to seal off the control ball chamber 72 from the outside atmosphere. The control ball chamber 72 is in communication with an internal passage-way, 78, which in turn is connected to the second outlet 66. The second outlet 66 is connected to a suitable conduit 80 which in turn is connected to the inlet of the second inflatable bladder 14. As was the case with the bladder 12, the bladder 14 is preferably connected to the conduit 80 through a conventional quick disconnect coupling 15. The coupling 15 may be identical to the coupling 13 and serves the purpose of trapping pressure in the bladder 14 for the purpose previously explained. The conduit 80, as was the case of the conduit 6B, is preferably at least partially flexible in order to allow ease of connection to the second inflatable bladder 14. A portion of the conduit 80 may be rigid in order to accommodate a softness control valve 82. The softness control valve 82 is preferable a solenoid type valve which is connected to the conduit 80. The softness control valve 82 could be a manually operated valve. The softness control valve 82 is normally closed and is opened in circumstance where it is desired to allow pressure to be released from the second bladder 14 which would have the effect of making the bladder 14 softer. The outlet of the softness control valve 82 is connected through a conduit 84 to a minimum softness control valve 86. The minimum softness control valve 86 is a valve which is pre-set to prevent the pressure in the upper bladder 14 from falling below a pre-selected level. This is done in order to prevent total collapse of the second inflatable bladder 14 during normal use. That is, the range of softness of the mattress 10 of the present invention does not allow for complete non-inflation of the bladder 14. The minimum release pressure of the softness control valve 86 may be varied. FIG. 7 illustrates that the minimum softness control valve 86 is the same general type of valve as that used for the maximum pressure control valve 50 in that an internal ball 88 of a pre-selected weight is used to control the pressure at which the valve will operate. As was previously explained, this pressure may be varied by inserting a spring to vary the pressure, or a line-pressure sensor could also be used to control the solenoid valve to allow activation of the solenoid valve only within a certain pressure range. However, the arrangement in FIG. 7 has proven to be quite satisfactory for normal usage. Thus, the operation of the circuit shown in FIG. 7 is such that a working fluid, preferably air, under pressure is furnished from the compressor 46 through the conduit 48 to the valve 50 through the conduit 54, through the valve 56 and through the conduit 58 to the differential pressure control valve 60. It then flows out directly through the conduit 68 and into the first inflatable bladder 12. Once the bladder 12 has started to inflate, it will begin to develop a back pressure on the ball 74 in the pressure control valve 60. At this point, the ball 74 will rise within the control ball chamber 72 and allow fluid under pressure to flow through the internal passage way 78 out the outlet 66 and through the conduit 80 into the second inflatable bladder 14. The second inflatable bladder 14 will then also inflate itself to a pre-selected level until it also begins to develop back pressure and forces the ball 74 back into its seat within the control chamber 72. It should be appreciated that because of the orifice size restrictions within the control ball chamber 72, the pressure in the upper or second inflatable bladder 14 will also be slightly less than the pressure in the lower or first inflatable bladder 12. This pressure differential can be controlled by adjusting the size of the orifices either in the inlet to the control valve chamber 72 or by controlling the diameter of the internal passage 78. Once these pressures have been established within the system, the compressor 46 may be shut down and would be needed only to maintain pressure should leakage occur within the system. After having been inflated to the maximum level, the softness of the second inflatable bladder 14 can be adjusted by opening the solenoid valve 82 which will allow some of the air to escape. This can continue until such as time as the pressure in the second bladder 14 has reached a level where it would be re-inflated because of the differential between the two bladders 12 and 14.

As was mentioned with respect to FIG. 5, a procedure pad 42 can also be used with this particular system, particularly since a source of working fluid is available through the compressor 46. A branch conduit 90 may be connected to the conduit 48, which is connected to the outlet of the air compressor 46. The conduit 90 may then be routed through the inlet of a solenoid valve 92 which then has an outlet connected to conduit 94 which is connected to the procedure pad 42. The solenoid valve 92 is of the normally closed type so that when it is activated, working fluid will be allowed to flow through the conduit 90 and 94 and inflate the procedure pad 42. This same branch arrangement could be used for other purposes such as the perforated bladder 44 shown in FIG. 6. This arrangement provides a second fluid circuit means that is selectively operable through the solenoid valve 92 to connect the compressor 46 to various fluid operated medical procedure devices. These devices can include the pad 42 and the perforated bladder 44.

Figure 8:
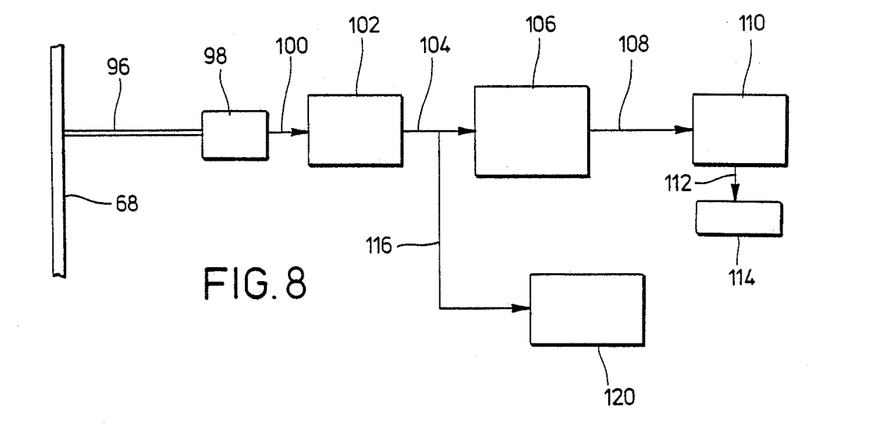
FIG. 8 is a block diagram of the occupant departure warning system of the present invention.

FIG. 8 illustrates in a block diagram form a third circuit means that is a bed exit system or occupant departure warning system which provides additional safety for a hospital patient using the present device. A branch conduit 96 is connected into the conduit 68 which furnishes operating fluid to the first inflatable bladder 12. Because the pressure in the first inflatable bladder 12 is always the highest pressure, it will be a relatively fixed pressure during the time that a patient occupies the air mattress of the present invention. The conduit 96 is attached to a pressure transducer 98 which will produce an electrical output signal proportional to the pressure presented to it by the conduit 96. The signal from the pressure transducer 98 may be transmitted along an electrical connector 100 to an amplifier 102 where the signal from the transducer 98 may be increased to a level which is more easily analyzed. The output of the amplifier 102 is connected through an electrical connector 104 to a signal processing circuit 106. The signal processing circuit 106 is one of the conventional type which will produce an output signal on an electrical connector 108 in response to a sudden drop in the input signal presented to it along connector 104. This in turn will indicate that there has been a sudden drop in the pressure sensed in the conduit 68. This will correspond to the departure of a patient from the mattress 10 of the present invention. Thus, the connector 108 will carry a signal to an alarm circuit 110 which in turn will send a signal through a connector 112 to a nurse call activator 114 which can be a visual or an audible warning signal such as a buzzer or a bell. It should also be noted that the output signal from the amplifier 102 could be connected through an electrical connector 116 to a readout device 120 to show the actual air pressure in the conduit 68. The readout device 120 can be a conventional dial, liquid crystal, or light emitting type display which would show the actual pressure in the inflatable bladder 12. This then could serve as a visual check on the proper operation of the maximum pressure valve 50 and of the differential pressure valve 60.

Figure 9:
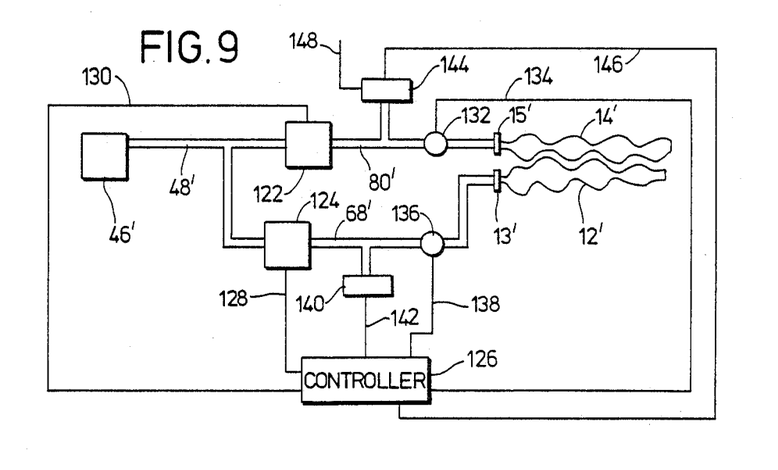
FIG. 9 is a block diagram of a modified fluid circuit of the present invention.

FIG. 9 illustrates a modified embodiment of the fluid control circuit of the present invention. The fluid control circuit shown in FIG. 7 is basically a mechanical valve system in which the differential pressure control valve 60 controls the differential pressure between the bladders 12 and 14 in a mechanical fashion. The electrical valve components in the control circuits shown in FIG. 7 are a convenience to allow easy patient control of the system. It is, however, possible to provide a completely electronically controlled system which provides some additional degree of flexibility in the operation of the present invention. This electronic embodiment of the control circuit is shown in FIG. 9. In FIG. 9, components which are in common with the embodiment shown on FIG. 7 are given the same reference numerals with the addition of a prime to allow an easier comparison of the two systems.

In FIG. 9, the air compressor 46' has an outlet conduit 48' with two branches which are connected to two electrically operated, normally closed solenoid valves 122 and 124. The functioning of the solenoid valves 122 and 124 is controlled through the operation of an electronic controller 126 which is connected to them through suitable electrical lines 128 and 130. The controller 126 is of the type well known in the art today which may be microprocessor based or may be a small general purpose digital computer. However, it is well within the skill of the art to provide control functions using such controllers as will be described. The outlet of the solenoid valve 122 is connected through a conduit 80' to the upper bladder 14' through the quick disconnect coupling 15' as previously described. Likewise, the solenoid valve 124 is connected through a conduit 68' and a quick disconnect coupling 13' to the lower bladder 12'. An additional element inserted in the conduit 80' is a pressure sensor 132 of the type known in the art which will generate an electrical signal proportional to the pressure which it senses. An electrical connector 134 presents the signal from the pressure sensor 132 to the controller 126. A similar electrical pressure sensor 136 is connected in the conduit 68' and has its signal connected through a connector 138 to the controller 126. The pressure sensors 132 and 136 are situated such that they will present a pressure signal which is a measure of the inflation pressure in the bladders 12' and 14' respectively. These signals are then fed to the controller 126 where they are compared with appropriate set points placed in the memory of the controller 126. That is, the controller 126 will have programmed into it a fixed set point differential between the pressures sensed by the pressure sensors 132 and 136. This function will again be identical to that described with respect to FIG. 7 in that the lower bladder 12' will always partially inflate before inflation of the upper bladder 14' is allowed to begin. Furthermore, the set points will be selected such that there will always be a preselected pressure differential between the pressure in the two bladders 12' and 14'. This differential may be adjusted in FIG. 7 by adjusting either the weight of the control ball 74 or perhaps spring loading the control ball 74. In the present case, this preset pressure differential may be adjusted by simply changing the command or the programming of the controller 126. The controller 126 will send signals to open and close the solenoid valves 122 and 124 in accordance with its preset pressure program in response to signals received from the pressure sensors 132 and 136. The operation, once the compressor 46 has started is that the solenoid valve 124 will always open first to allow pressure to begin to develop in the lower bladder 12'. Once a preselected pressure has been reached, the solenoid valve 122 may be opened to allow inflation of the upper bladder 14' to begin. Once the present pressure differential between the bladders 12' and 14' has been reached, the valve 122 may be closed or both valves may be closed depending upon their relative pressure situations at that time. A solenoid valve 140 is connected to the conduit 68' in order to provide a maximum firmness control function. In this respect, the valve 140 is analogous to the valve 50 described in FIG. 7 which is a maximum pressure control valve. The solenoid valve 140 is controlled through an electrical line 142 by the controller 126. If the pressure sensor 136 reports to the controller 126 a pressure in the bladder 12' which is beyond the maximum allowed pressure, then a signal will be transmitted to the solenoid valve 140 to allow the solenoid valve 140 to open and vent or relieve pressure from the bladder 12'. This is precisely the same function as provided by the pressure relief valve 50 in FIG. 7. Similarly, a firmness control solenoid valve 144 is provided in conduit 80'. The valve 144 is connected to the controller 126 through an electrical wire 146 and also may be controlled by a bed occupant through electrical wiring 148. The valve 144 may be operated by an occupant of the bed to control the feel or firmness of the upper bladder 14'. In this respect, valve 144 is analogous to the softness control valve 82 described with respect to FIG. 7. The controller 126 has built into it a limit which will prevent the valve 144 from being operated if the pressure sensed by the pressure sensor 132 is too low. It might be pointed out that the minimum softness control valve 86 in FIG. 7 performs basically this same function. Thus, it can be seen that FIG. 9 presents a somewhat modified electric control circuit for the present invention, but is very much analogous to the control circuit previously described in FIG. 7. The choice of which of these two embodiments to use is largely a matter of convenience, expense and ultimate application of the bed of the present invention.

Figure 10:
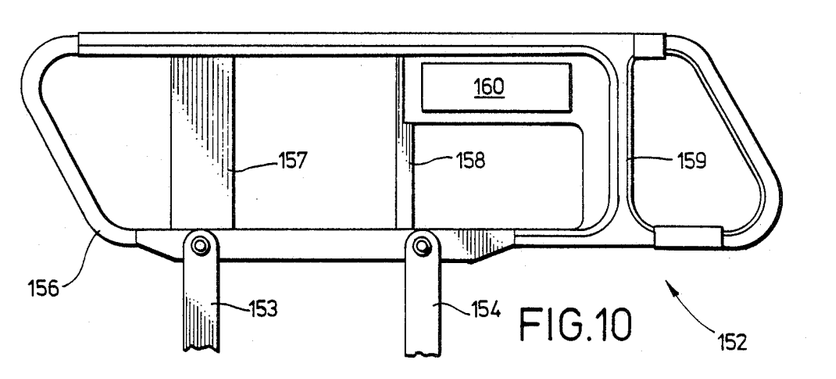
FIG. 10 is a partial elevation view of a sideguard for a hospital bed, the sideguard including a bed function control panel.

FIG. 10 shows a sideguard 152 of the type normally used with hospital beds. The sideguard 152 is of the half length type and there would normally be two such guards 152 on each side of a bed. The mattress 10 of the present invention can be used with hospital beds which have this type of sideguard 152. The sideguard 152 is attached to the bed through support brackets 153 and 154. These are connected to allow a pivoting up and down motion of the sideguard 52. The sideguard 152 has a generally continuous perimeter member 56 which is connected by web member 157, 158 and 159. A bed control panel 160 is positioned between the web members 158 and 159.

Figure 11:
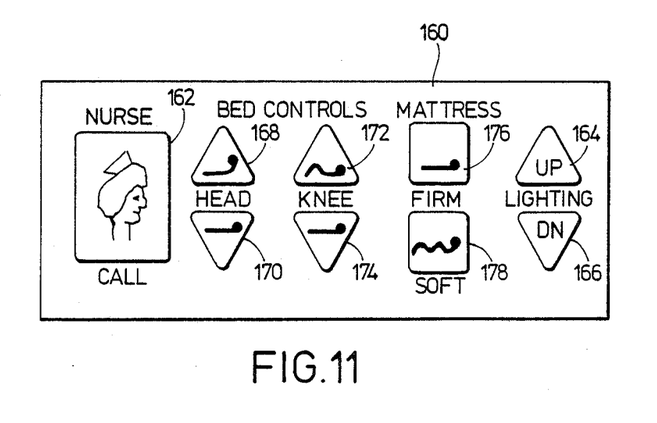
FIG. 11 is a plan view of the bed function control panel from the sideguard of FIG. 10.

FIG. 11 shows the bed control panel 160 in more detail. The bed control panel 160 carries a member of electrical switches which are operable by the bed occupant. The type of system per se is well known in the art. In this case, a nurse call switch 162 will activate a signal at the nursing station when pressed. Lighting switches 164 and 166 will control the room and overbed lights. A head up switch 168 will cause the head of the bed to raise and a head down switch 170 will cause the head to lower. A knee up switch 172 will raise the thigh/knee position of the bed while a knee down switch 174 will cause the knee portion to lower. Actuation of a firm switch 176 will turn on the compressor 46 and open the valve 56 (in FIG. 7) or the controller 126 (in FIG. 9). This will allow inflation of the bladders 12 and 14 (or 12' and 14') within the prescribed limits of the control system in use. Conversely. activation of a soft switch 178 will allow air to bleed from the bladders 12 and 14 (or 12' and 14') by opening the valve 82 or 144. As was the case with the inflation or increasing firmness mode, the softness mode will operate within the prescribed limits of the control system in use, two possible modes having been shown in FIGS. 7 and 9.

What is claimed is:

1. An improved inflatable bed system which comprises:
    (A) A first inflatable bladder positioned to be distal from a person who lies on said bed;
    (B) A second inflatable bladder positioned in contacting proximity to said first inflatable bladder and located proximate to said first inflatable bladder and located proximate to a person who lies on said air bed;
    (C) Means for holding said first and second inflatable bladders together so that they co-operate as a unit;
    (D) A source of inflating fluid providing a pressure sufficient to inflate said first and second inflatable bladders to the degree necessary to support a person lying on said first and second inflatable bladders; and
    (E) Fluid circuit means, operatively connecting said source of inflating fluid and said first and second inflatable bladders for controlling the flow of said inflating fluid, said fluid circuit means including a differential pressure valve having a single inlet connected to said source of inflating fluid and having two outlets, one of said outlets being connected to said first inflatable bladder and the other of said two outlets being connected to said second inflatable bladder such that a pre-selected pressure differential is maintained between said first and second inflatable bladders and the first inflatable bladder is always at least partially inflated before inflation of said second bladder begins.

2. The system of claim 1 wherein said differential pressure valve is configured such that said second outlet will remain closed until said first inflatable bladder is inflated to a pre-selected fluid pressure and said second outlet will open in response to the attainment of said pre-selected fluid pressure to thereby allow flow of inflating fluid to said second inflatable bladder.

3. The system of claim 2 wherein said pre-selected fluid pressure of said differential pressure valve will maintain a fixed pressure differential between said first and second inflatable bladders.

4. The system of claim 2 wherein said fluid circuit means further includes a maximum firmness control valve, connected in circuit between said source of inflating fluid and said differential pressure control valve, said maximum firmness control valve having a pre-selected pressure relief point such that exceeding said pre-selected pressure relief point will cause venting of said inflating fluid from said fluid circuit thereby limiting the pressure supplied to said first and second inflatable bladders.

5. The system of claim 2 wherein said fluid circuit means further includes a softness control valve connected to said second outlet of said differential pressure valve such that inflating fluid furnished to said second bladder normally bypasses said softness control valve, said softness control valve being selectively operable to allow release of pressure from said second inflatable bladder from an outlet of said softness control valve.

6. The system of claim 5 wherein said fluid circuit means further includes a minimum softness control valve connected to the outlet of said softness control valve and having a pre-selected pressure release set point such that the minimum allowable pressure in said second inflatable bladder is controlled by the pre-selected pressure release point of said minimum softness control valve.

7. The system of claim 1 which further includes a second fluid circuit means operably connected to said source of inflating fluid, said second fluid circuit means including a selectively operable, normally closed valve, connected to said source of inflating fluid, and a fluid operated medical procedure device connected to an outlet of said normally closed valve, said medical procedure device being activated when said normally closed valve is opened to allow flow of said inflating fluid to said medical procedure device.

8. The system of claim 7 wherein said medical procedure device is an inflatable pad positioned with respect to said first and second inflatable bladders such that inflation of said inflatable pad will raise at least a portion of said first and second inflatable bladders to a pre-selected position.

9. The system of claim 7 wherein said inflating fluid is a gas and wherein said medical procedure device is a perforated bladder, having a plurality of openings on one side thereof to allow escape of said gas, and positioned such that a person lying on said bed will be washed by the flow of gas from said perforated bladder.

10. The system of claim 1 which further includes a third circuit means connected to said first inflatable bladder, responsive to the pressure in said first inflatable bladder for generating a warning signal in response to a drop in pressure in said first inflatable bladder, said drop in pressure serving as an indicia that a person occupying said air bed has left said air bed.

11. The system of claim 10 wherein said third circuit means includes:
(A) A pressure transducer connected to said first inflatable bladder for generating an electrical output signal proportional to the fluid pressure in said first inflatable bladder;
(B) An amplifier connected to said electrical output signal of said pressure transducer for increasing the level of said electrical output signal;
(C) A signal processing circuit, connected to said amplifier and responsive to said electrical output signal, for generating an output warning signal in response to said electrical output signal reaching a pre-selected value, said pre-selected value being chosen to represent the pressure in said bed when said bed is unoccupied; and
(D) Warning means, connected to said output warning signal, for generating a warning signal in response to the receipt of said output warning signal.

12. The inflatable bed system of claim 1 wherein said means for holding said first and second inflatable bladders together includes:
(A) A lower casing portion of a generally open box shape having upstanding sidewalls connected to a base portion, said first and second inflatable bladders being placed in overlapping alignment within said sidewalls, the perimeter of said lower casing portion being substantially equal to the perimeter of said first and second inflatable bladders and the depth of said sidewalls being slightly greater than the overall combined depth of said first and second inflatable bladders in their fully inflated state; and
(B) An upper casing portion connected to the perimeter of the open end of said upstanding sidewalls to thereby contain said first and second inflatable bladders completely within said upper and lower casing portions, said first and second inflatable bladders having means extending through said lower casing to allow introduction of inflating fluid to said first and second inflatable bladders.

13. The system of claim 12 which further includes:
(A) A first foam pad, positioned on said base portion and onto which said first and second inflatable bladders are placed; and
(B) A second foam pad positioned in overlying relationship to said second inflatable bladder.

14. The system of claim 13 which further includes a needle barrier sheet, substantially co-extensive with said second foam pad and said second inflatable bladder and positioned between said second foam pad and said second inflatable bladder, protecting said second inflatable bladder from accidental puncture by medical procedure needles which miss their intended target and enter said bed system.

15. The system of claim 12 wherein said the perimeter of said lower casing portion is greater than the perimeter of said first and second inflatable bladders and further including a foam perimeter pad filling the resulting space between the upstanding sidewalls of said casing and said first and second inflatable bladders.

16. The system of claim 15 wherein said foam perimeter pad includes an upper tapered portion that tapers away from said sidewalls and said second inflatable bladder includes a corresponding reverse tapered portion to present a barrier to needle entry into said second inflatable bladder from said sidewalls.

17. A method for controlling the firmness of an inflatable bed which comprises the steps of:
(A) positioning a first inflatable bladder distal from a person lying on said bed;
(B) positioning a second inflatable bladder proximate to a person lying on said bed and in overlying contacting location with respect to said first inflatable bladder;
(C) providing a source of inflating fluid under pressure;
(D) inflating said first bladder with said inflating fluid to a first pre-selected pressure level;
(E) preventing the inflation of said second inflatable bladder until said first pre-selected pressure level is achieved;
(F) continuing the inflation of said first inflatable bladder to its final pressure which is greater than said first pre-selected pressure level;
(G) inflating said second inflatable bladder to its final pressure which is a pre-selected fixed percentage of the final pressure in said first inflatable bladder; and
(H) venting pressure from said second inflatable bladder to adjust the firmness of said second inflatable bladder.

18. The method of claim 17 which further includes the steps of:
(A) sensing the pressure in said first inflatable bladder;
(B) generating an electrical signal in response thereto that is preparation to the pressure in said first inflatable bladder;
(C) comparing said electrical signal with a pre-selected signal level that is indicative of the signal present when said bed is unoccupied; and
(D) generating a warning signal in response to the electrical signal proportional to the pressure in said first inflatable bladder reaching said pre-selected signal level.

19. An improved inflatable bed system which comprises:
(A) a first inflatable bladder positioned to be distal from a person who lies on said bed;
(B) a second inflatable bladder positioned in contacting proximity to said first inflatable bladder and located proximate to said first inflatable bladder and located proximate to a person who lies on said bed;
(C) means for holding said first and second inflatable bladders together so that they co-operate a unit;
(D) a source of inflating fluid providing a pressure sufficient to inflate said first and second inflatable bladders to the degree necessary to support a person lying on said first and second inflatable bladders;
(E) fluid circuit means, operatively connecting said source of inflating fluid and said first and second inflatable bladders for controlling the flow of said inflating fluid, said fluid circuit means including an electronic controller operatively connected to open and close valves interconnecting said first and second inflatable bladders and said source of inflating fluid to allow said inflating fluid to be furnished to said first and second inflatable bladders, said fluid circuit means further including pressure sensors connected to said electronic controller and sensing the pressure of said inflating fluid in said first and second inflatable bladders, said electronic said first and second inflatable bladders, said electronic controller being set to open and close said valves such that a pre-selected pressure differential is maintained between said first and second inflatable bladders and the first inflatable bladder is always at least partially inflated before inflation of said second bladder begins.

20. The system of claim 19 wherein said fluid circuit means further includes a softness control valve connected to said second inflatable bladder and said electronic controller, said softness control valve being selectively operable to allow release of pressure from said second inflatable bladder from an outlet of said softness control valve, said electronic controller having a pre-selected pressure release set point such that the minimum allowable pressure in said second inflatable bladder is controlled by the pre-selected pressure release point for said minimum softness control valve.

21. The inflatable bed system of claim 19 wherein said means for holding said first and second inflatable bladders together includes:

(A) a lower casing portion of a generally open box shape having upstanding sidewalls connected to a base portion, said first and second inflatable bladders being placed in overlapping alignment within said sidewalls, the perimeter of said lower casing portion being substantially equal to the perimeter of said first and second inflatable bladders and the depth of said sidewalls being slightly greater than the overall combined depth of said first and second inflatable bladders in their fully inflated state; and (B) an upper casing portion connected to the perimeter of the open end of said upstanding sidewalls to thereby contain said first and second inflatable bladders within said upper and lower casing portions, said first and second inflatable bladders having means extending through said lower casing to allow introduction of inflating fluid to said first and second inflatable bladders.

22. The new system of claim 21 which further includes:

(A) a first foam pad, positioned on said base portion and onto which said first and second inflatable bladders are placed; and (B) a second foam pad positioned in overlying relationship to said second inflatable bladder.

23. The system of claim 22 which further includes a needle barrier sheet, substantially co-extensive with said second foam pad and said second inflatable bladder and positioned between said second foam pad and said second inflatable bladder, protecting said second inflatable bladder from accidental puncture by medical procedure needles which miss their intended target and enter said bed system.

24. The system of claim 21 wherein said the perimeter of said lower casing portion is greater than the perimeter of said first and second inflatable bladders and further including a foam perimeter pad filling the resulting space between the upstanding sidewalls of said casing and said first and second inflatable bladders.

25. The system of claim 24 wherein said foam perimeter pad includes an upper tapered portion that tapers away from said sidewalls and said second inflatable bladder includes a corresponding reverse tapered portion to present a barrier to needle entry into said second inflatable bladder from said sidewalls.

26. The system of claim 19 which further includes a second fluid circuit means operably connected to said source of inflating fluid, said second fluid circuit means including a selectively operable, normally closed valve, connected to said source of inflating fluid, and a fluid operated medical procedure device connected to an outlet of said normally closed valve, said medical procedure device being activated when said normally closed valve if opened to allow flow of said inflating fluid to said medical procedure device.

27. The system of claim 26 wherein said medical procedure device is an inflatable pad positioned with respect to said first and second inflatable bladders such that inflation of said inflatable pad will raise at least a portion of said first and second inflatable bladders to a pre-selected position.

28. The system of claim 26 wherein said inflating fluid is a gas and wherein said medical procedure device is a perforated bladder, having a plurality of openings on one side thereof to allow escape of said gas, and positioned such that a person lying on said bed will be washed by the flow of gas from said perforated bladder.

* * * * *